(12) United States Patent
Binder, Jr. et al.

(10) Patent No.: US 7,357,804 B2
(45) Date of Patent: Apr. 15, 2008

(54) QUICK-RELEASE DRILL-GUIDE ASSEMBLY FOR BONE-PLATE

(75) Inventors: Lawrence J. Binder, Jr., Langhorne, PA (US); Christopher J. Ryan, West Chester, PA (US)

(73) Assignee: Synthes (U.S.A.), West Chester, PA (US)

( * ) Notice: Subject to any disclaimer, the term of this patent is extended or adjusted under 35 U.S.C. 154(b) by 697 days.

(21) Appl. No.: 10/639,515

(22) Filed: Aug. 13, 2003

(65) Prior Publication Data

US 2005/0038444 A1 Feb. 17, 2005

(51) Int. Cl.
*A61B 17/58* (2006.01)
(52) U.S. Cl. ............................................. 606/96
(58) Field of Classification Search .................. 606/96, 606/69, 79, 80, 86, 98, 104; 600/219, 220, 600/221, 226, 234
See application file for complete search history.

(56) References Cited

U.S. PATENT DOCUMENTS

| | | | |
|---|---|---|---|
| 831,592 A * | 9/1906 | Ballard | ........................ 600/221 |
| 1,831,813 A | 11/1931 | Levedahl | |
| 2,181,746 A | 11/1939 | Siebrandt | |
| 2,200,120 A | 5/1940 | Nauth | |
| 2,424,485 A | 7/1947 | Miller | |
| 2,494,229 A | 1/1950 | Collison | |
| 2,607,339 A | 8/1952 | Price | |
| 2,670,637 A | 2/1954 | Edmunds | |
| 2,674,906 A | 4/1954 | Timpner | |
| 3,071,030 A | 1/1963 | Larry | |
| 3,540,322 A | 11/1970 | Swanson | |
| 3,727,611 A | 4/1973 | Schultz | |
| 4,119,092 A | 10/1978 | Gil | |
| 4,388,921 A | 6/1983 | Sutter et al. | |
| 4,450,835 A | 5/1984 | Asnis et al. | |
| 4,493,317 A | 1/1985 | Klaue | |
| 4,646,413 A | 3/1987 | Nall et al. | |
| 4,668,134 A | 5/1987 | Vindez | |
| D291,246 S | 8/1987 | Lower | |
| 4,744,353 A | 5/1988 | McFarland | |
| 4,787,377 A | 11/1988 | Laboureau | |
| 4,788,970 A | 12/1988 | Karas et al. | |
| 4,791,918 A | 12/1988 | Von Hasselbach | |
| 4,803,976 A | 2/1989 | Frigg et al. | |
| 4,872,451 A | 10/1989 | Moore et al. | |
| 4,898,502 A | 2/1990 | Becher | |
| 4,911,153 A | 3/1990 | Border | |
| 4,941,781 A | 7/1990 | Becher | |
| 4,969,781 A | 11/1990 | Fahrner et al. | |
| 5,026,376 A | 6/1991 | Greenberg | |
| 5,030,219 A | 7/1991 | Matsen, III et al. | |

(Continued)

FOREIGN PATENT DOCUMENTS

CH 655646 A5 5/1986

(Continued)

*Primary Examiner*—Eduardo C. Robert
*Assistant Examiner*—David Comstock
(74) *Attorney, Agent, or Firm*—Stroock & Stroock & Lavan LLP

(57) ABSTRACT

A surgical drill-guide assembly can be releasably attached to a part of a bone-fixation system, for example, a plate. The surgical drill-guide assembly is used for example, to guide a drill, screw, bone fastener, or other instrument or fastener into bone.

38 Claims, 14 Drawing Sheets

U.S. PATENT DOCUMENTS

| | | |
|---|---|---|
| 5,054,968 A | 10/1991 | Eckman |
| 5,071,293 A | 12/1991 | Wells |
| 5,112,336 A | 5/1992 | Krevolin et al. |
| 5,133,720 A | 7/1992 | Greenberg |
| 5,147,367 A | 9/1992 | Ellis |
| 5,154,720 A | 10/1992 | Trott et al. |
| 5,207,753 A | 5/1993 | Badrinath |
| 5,250,055 A | 10/1993 | Moore et al. |
| 5,281,056 A | 1/1994 | Lawson et al. |
| 5,306,278 A | 4/1994 | Dahl et al. |
| 5,312,412 A | 5/1994 | Whipple |
| 5,324,295 A | 6/1994 | Shapiro |
| 5,364,399 A | 11/1994 | Lowery et al. |
| D357,534 S | 4/1995 | Hayes |
| 5,409,493 A | 4/1995 | Greenberg |
| D359,557 S | 6/1995 | Hayes |
| 5,423,826 A | 6/1995 | Coates et al. |
| 5,429,641 A | 7/1995 | Gotfried |
| 5,437,677 A | 8/1995 | Shearer et al. |
| 5,458,602 A | 10/1995 | Goble et al. |
| 5,484,446 A | 1/1996 | Burke et al. |
| 5,507,801 A | 4/1996 | Gisin et al. |
| 5,575,794 A | 11/1996 | Walus et al. |
| 5,584,839 A | 12/1996 | Gieringer |
| 5,595,193 A | 1/1997 | Walus et al. |
| 5,601,550 A | 2/1997 | Esser |
| 5,601,553 A | 2/1997 | Trebing et al. |
| 5,624,447 A | 4/1997 | Myers |
| 5,634,927 A | 6/1997 | Houston et al. |
| 5,637,112 A | 6/1997 | Moore et al. |
| D382,056 S | 8/1997 | Kammerer |
| 5,669,915 A | 9/1997 | Caspar et al. |
| 5,676,666 A | 10/1997 | Oxland et al. |
| 5,700,267 A | 12/1997 | Urbanski |
| 5,722,978 A | 3/1998 | Jenkins, Jr. |
| 5,725,532 A | 3/1998 | Shoemaker |
| 5,741,266 A | 4/1998 | Moran et al. |
| 5,743,916 A | 4/1998 | Greenberg et al. |
| 5,746,743 A | 5/1998 | Greenberg |
| 5,746,763 A | 5/1998 | Benderev et al. |
| 5,749,884 A | 5/1998 | Benderev et al. |
| 5,755,721 A | 5/1998 | Hearn |
| 5,766,221 A | 6/1998 | Benderev et al. |
| 5,769,856 A | 6/1998 | Dong et al. |
| D397,220 S | 8/1998 | Kumar et al. |
| D398,996 S | 9/1998 | Simmons et al. |
| 5,836,950 A | 11/1998 | Hansson |
| RE36,020 E | 12/1998 | Moore et al. |
| 5,851,207 A | 12/1998 | Cesarone |
| D404,126 S | 1/1999 | Asfora |
| 5,888,034 A | 3/1999 | Greenberg |
| 5,895,390 A | 4/1999 | Moran et al. |
| 5,910,143 A | 6/1999 | Cripe et al. |
| 5,913,860 A | 6/1999 | Scholl |
| 5,938,686 A | 8/1999 | Benderev et al. |
| 5,947,654 A | 9/1999 | Blankenship et al. |
| 5,951,561 A | 9/1999 | Pepper et al. |
| 5,954,722 A | 9/1999 | Bono |
| 5,957,927 A | 9/1999 | Magee et al. |
| 5,961,257 A | 10/1999 | Bettini et al. |
| 5,961,530 A | 10/1999 | Moore et al. |
| 6,007,535 A | 12/1999 | Rayhack et al. |
| 6,013,083 A | 1/2000 | Bennett |
| 6,019,767 A | 2/2000 | Howell |
| 6,036,696 A | 3/2000 | Lambrecht et al. |
| 6,059,789 A | 5/2000 | Dinger et al. |
| 6,066,142 A | 5/2000 | Serbousek et al. |
| 6,113,637 A | 9/2000 | Gill et al. |
| 6,139,550 A | 10/2000 | Michelson |
| D433,506 S | 11/2000 | Asfora |
| 6,143,012 A | 11/2000 | Gausepohl |
| 6,152,927 A | 11/2000 | Farris et al. |
| 6,193,721 B1 | 2/2001 | Michelson |
| 6,193,723 B1 | 2/2001 | Cripe et al. |
| 6,206,886 B1 | 3/2001 | Bennett |
| 6,210,415 B1 | 4/2001 | Bester |
| 6,235,034 B1 | 5/2001 | Bray |
| 6,238,400 B1 | 5/2001 | Bays |
| 6,241,729 B1 | 6/2001 | Estes et al. |
| 6,258,091 B1 | 7/2001 | Sevrain et al. |
| 6,283,969 B1 | 9/2001 | Grusin et al. |
| 6,287,313 B1 | 9/2001 | Sasso |
| 6,299,616 B1 | 10/2001 | Beger |
| 6,306,139 B1 | 10/2001 | Fuentes |
| 6,330,845 B1 | 12/2001 | Meulink |
| 6,342,056 B1 | 1/2002 | Mac-Thiong et al. |
| 6,342,057 B1 | 1/2002 | Brace et al. |
| 6,361,537 B1 | 3/2002 | Anderson |
| 6,371,959 B1 | 4/2002 | Trice |
| 6,379,364 B1 | 4/2002 | Brace et al. |
| 6,383,186 B1 | 5/2002 | Michelson |
| 6,398,783 B1 | 6/2002 | Michelson |
| 6,416,518 B1 | 7/2002 | DeMayo |
| 6,416,528 B1 | 7/2002 | Michelson |
| 6,419,678 B1 | 7/2002 | Asfora |
| 6,428,542 B1 | 8/2002 | Michelson |
| 6,436,103 B1 | 8/2002 | Suddaby |
| 6,447,512 B1 | 9/2002 | Landry et al. |
| 6,454,771 B1 | 9/2002 | Michelson |
| 6,475,190 B2 | 11/2002 | Young |
| 6,491,714 B1 | 12/2002 | Bennett |
| 6,524,238 B2 | 2/2003 | Velikaris et al. |
| 6,524,312 B2 | 2/2003 | Landry et al. |
| 6,527,776 B1 | 3/2003 | Michelson |
| 6,533,786 B1 | 3/2003 | Needham et al. |
| 6,558,089 B2 | 5/2003 | DeBlasio |
| 6,562,046 B2 | 5/2003 | Sasso |
| 6,565,571 B1 | 5/2003 | Jackowski et al. |
| 2001/0027320 A1 | 10/2001 | Sasso |
| 2001/0047172 A1 | 11/2001 | Foley et al. |
| 2002/0004661 A1 | 1/2002 | Sevrain et al. |
| 2002/0022847 A1 | 2/2002 | Ray, III et al. |
| 2002/0045896 A1 | 4/2002 | Michelson |
| 2002/0082606 A1 | 6/2002 | Suddaby |
| 2002/0120273 A1 | 8/2002 | Needham et al. |
| 2002/0128655 A1 | 9/2002 | Michelson |
| 2002/0133172 A1 | 9/2002 | Lambrecht et al. |
| 2002/0147450 A1 | 10/2002 | LeHuec et al. |
| 2002/0183754 A1 | 12/2002 | Michelson |
| 2003/0018335 A1 | 1/2003 | Michelson |
| 2003/0040748 A1 | 2/2003 | Aikins et al. |
| 2003/0040752 A1 | 2/2003 | Kitchens |
| 2003/0040753 A1 | 2/2003 | Daum et al. |
| 2003/0045880 A1 | 3/2003 | Michelson |
| 2003/0055430 A1 | 3/2003 | Kim |
| 2003/0083661 A1 | 5/2003 | Orbay et al. |
| 2003/0083667 A1 | 5/2003 | Ralph et al. |

FOREIGN PATENT DOCUMENTS

| | | |
|---|---|---|
| DE | 3222037 A1 | 4/1984 |
| DE | 4238582 A1 | 5/1994 |
| EP | 281763 A2 | 9/1988 |
| EP | 495488 A2 | 1/1991 |
| EP | 506213 A1 | 2/1991 |
| EP | 518071 A1 | 12/1992 |
| EP | 591985 A1 | 4/1994 |
| EP | 518071 B1 | 10/1994 |
| EP | 281763 B1 | 12/1998 |
| EP | 962190 A2 | 12/1999 |
| EP | 995403 A1 | 4/2000 |
| EP | 1132052 A2 | 9/2001 |
| FR | 2713473 A1 | 6/1995 |
| FR | 2735008 A1 | 12/1996 |

| | | | |
|---|---|---|---|
| FR | 2784570 A1 | 4/2000 |
| GB | 2243316 A | 10/1991 |
| GB | 2324967 A | 11/1998 |
| JP | 2236331 A | 9/1990 |
| JP | 5031116 A | 2/1993 |
| JP | 10-328205 A | 12/1998 |
| JP | 2001-245894 A | 9/2001 |
| WO | WO93/19678 A2 | 10/1993 |
| WO | WO95/11632 A1 | 5/1995 |
| WO | WO96/05778 A1 | 2/1996 |
| WO | WO96/15727 A1 | 5/1996 |
| WO | WO96/20650 A1 | 7/1996 |
| WO | WO98/34553 A1 | 8/1998 |
| WO | WO99/21502 A1 | 5/1999 |
| WO | WO99/52453 A2 | 10/1999 |
| WO | WO 01/01874 A1 | 1/2001 |
| WO | WO 02/02999 A1 | 1/2002 |
| WO | WO 02/080791 A1 | 10/2002 |
| WO | WO 03/007826 A1 | 1/2003 |

\* cited by examiner

QUICK-RELEASE DRILL-GUIDE ASSEMBLY FOR BONE-PLATE

FIELD OF THE INVENTION

The present invention relates to a surgical drill-guide assembly that can be releasably attached to a part of a bone-fixation system, for example, a bone plate. The surgical drill-guide assembly of the present invention is used for example, to guide a drill-bit, screw, bone fastener, or other instrument or fastener into bone or other tissue.

BACKGROUND

The use of surgical fixation plates for a variety of orthopedic applications is widely accepted. The plates are used by surgeons or users to stabilize, mend, or align a patient's bone as well as alter compression of patient's bones. Plates are typically fastened to the bones with a plurality of fasteners such as screws that are installed through holes in the plate. Proper orientation and alignment of fasteners and secure surgical fixation of the plates can mitigate some of the potential future complications after implantation.

Bone plates used, for example, in spinal applications must be installed with special care, as the plates may be used for long-term, intervertebral fixation, bone-fragment fixation, and/or anterior decompression in the cervical region of the spine. The margin for error in spinal surgery is quite small, particularly because of the sensitivity of the spinal cord and the risk inherent with invasive procedures around the spinal cord. In particular, the dimensions of vertebral bone available for setting fasteners are fairly limiting.

Each fixation screw should properly align with its associated plate hole so that each screw is seated correctly with the plate and enters the bone at an appropriate angle. Any misalignment of the screw within the plate hole risks tissue damage and spinal cord injury. In addition, improperly seated screws may result in an unstable or insecure connection of the plate to the bony material, thus potentially defeating the usefulness of the plate. Locking plates, in particular, demand precise fastener alignment.

SUMMARY OF THE INVENTION

The present invention relates to a drill-guide assembly, which in one embodiment comprises an alignment drill-barrel, a bushing, a dual-arm support, a ratchet-gear mechanism, a handle member, and a release knob.

The alignment drill-barrel has a proximal end and a forward-end also called the distal end. The proximal end of the alignment drill-barrel preferably has two ridges, and the distal end is generally tapered. The alignment drill-barrel is configured to receive and guide a drill-bit, bone tap, screw, bone fastener or other instrument into bone or other tissue. The alignment drill-barrel preferably allows for the passage of fixation pins or bone screws, drills, taps, or awls through it in a predetermined trajectory.

The bushing preferably has a radially expandable forward-end and a proximal end, wherein the forward-end is configured to engage a fastener hole in a bone-plate. The radially expandable forward end of the bushing preferably has a plurality of finger portions. The radially expandable forward end also preferably has a shoulder, neck, and an outwardly projecting rim disposed forward of the neck. The bushing is configured to slidably receive the alignment drill-barrel. Sliding the alignment drill-barrel toward the forward end of the bushing preferably expands the forward end of the bushing to secure the drill-guide assembly in a bone-plate.

The dual-arm support in one embodiment is generally "L-shaped" with the two ends of the "L" forming an obtuse angle. The dual-arm support preferably has a space provided in its center region. In one embodiment, the end portion, which is generally horizontally disposed, comprises a pivot-hole for inserting a pivot screw. At one end, the dual-arm support is immovably or fixedly connected to the proximal end of the bushing, while at its other end, the dual-arm support is immovably connected to the front end of the handle member.

The handle member in an exemplary embodiment has a front end and a back end. It is generally oval shaped with broad grooves on top to provide better grip for the surgeon or user using the drill-guide assembly. The handle may be hollow or solid depending upon design choice.

The ratchet-gear mechanism in one embodiment is generally "Y-shaped" and is housed within the space of the dual-arm support. At one end, the first leg of the ratchet-gear mechanism is pivotably connected to the dual-arm support at a pivot-point. That end of the first leg further extends beyond the pivot point forming a C-shaped vice-grip. The C-shaped vice-grip attaches to the alignment drill-barrel. The C-shaped vice-grip grasps the alignment drill-barrel in between the two ridges at the proximal end. In a preferred embodiment, the plane of the C-shaped vice-grip is generally perpendicular to the axial direction of the alignment drill-barrel, and the bushing. The second leg of the Y-shaped ratchet-gear mechanism comprises pawls on the outer side which permit incremental swiveling of the ratchet-gear mechanism in a plane perpendicular to the plane of C-shaped vice-grip. The tail-end of the Y-shaped ratchet-gear mechanism acts as a trigger and generally moves in a rotational motion relative to the pivot point in a direction toward or away from the handle member. Movement of the ratchet-gear mechanism, and particularly the C-shaped vice grip, slides the alignment drill-barrel relative to the bushing.

The release knob in an exemplary embodiment has a curved longitudinal member with a base. The base has serrations on one side of its circumferential border and a hole on the other side. The release knob is pivoted through the hole in the base about a dowel pin that is attached to the dual-arm support.

When the tail of the Y-shaped ratchet-gear mechanism is pressed by a finger of a user in a rotary motion in a direction toward the handle member, the distal end of the alignment drill-barrel is urged into the bushing which in turn, expands the forward-end of the bushing, thus locking the bushing within the fastener hole of the bone-plate. The bushing is configured and dimensioned to expand within the bone-plate fastener holes such that it is releasably locked to the bone-plate.

When the Y-shaped ratchet-gear mechanism engages the release knob, the pawls on the outer surface of the second leg of the Y-shaped ratchet-gear mechanism engage the serrations on the release knob to lock the drill-guide to the bone-plate. The alignment drill-barrel preferably self-aligns with the axis of the fastener hole in the plate.

When the release knob is further pressed, the pawls are disengaged from the serrations, and the Y-shaped ratchet-gear mechanism returns to an unactuated position, preferably by action of a biasing member such as a spring. The Y-shaped ratchet-gear mechanism, in turn, through its C-shaped vice-grip moves the alignment drill-barrel in a longitudinal direction along its axis, away from the fingers.

As a result, the bushing assumes a retracted position thereby disengaging the fastener hole.

BRIEF DESCRIPTION OF THE DRAWINGS

Preferred features of the present invention are disclosed in the accompanying drawings, wherein similar reference characters denote similar elements throughout the several views. While the presentation is desired and its features presented according to certain illustrated embodiments it is to be understood that the invention is not so limited to the particular embodiments shown and described, wherein.

DETAILED DESCRIPTION OF THE PREFERRED EMBODIMENTS

Figure 1:
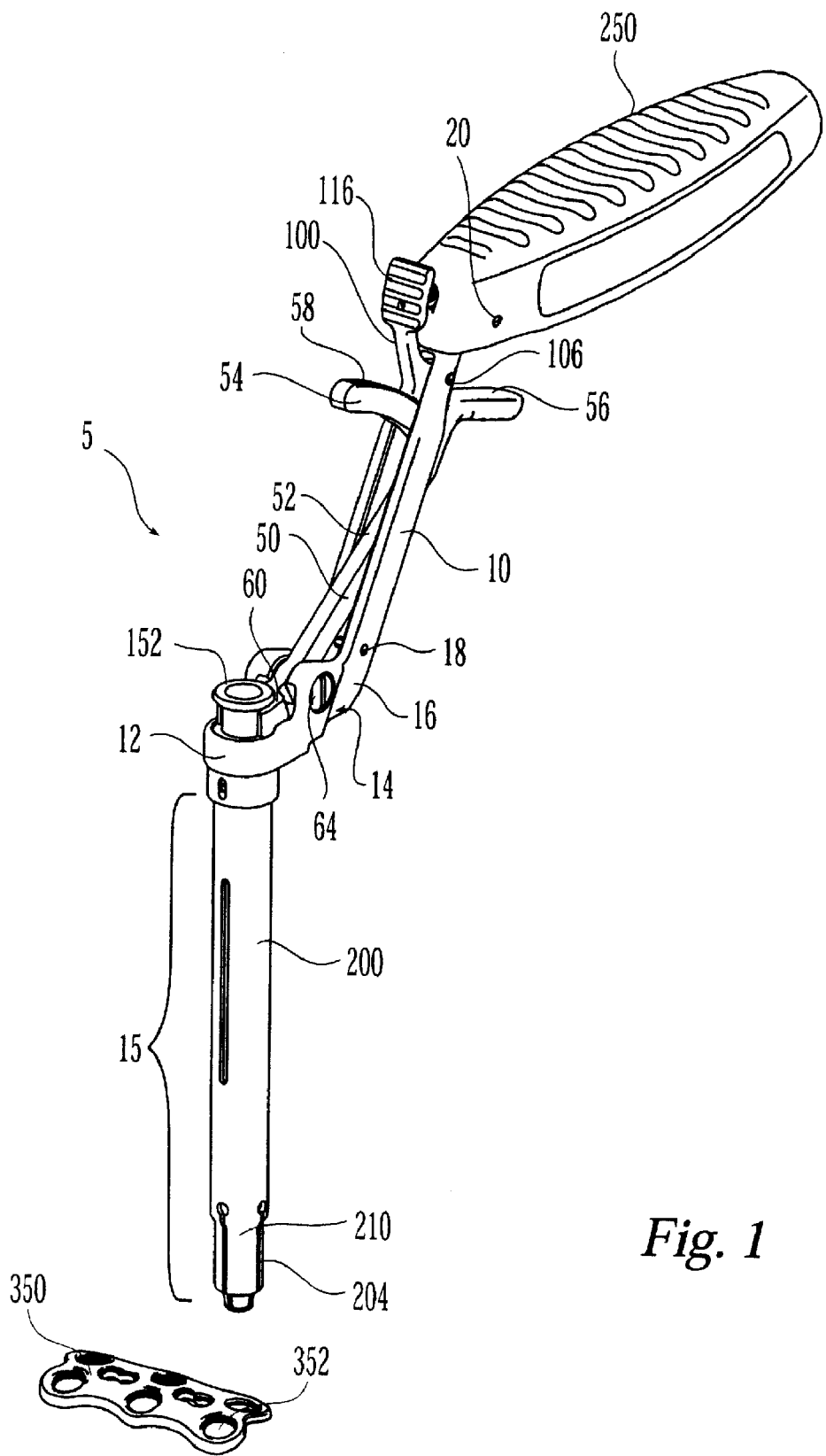
FIG. 1 is a perspective view of the drill-guide assembly.

Referring to FIG. 1, there is shown an exemplary surgical drill-guide assembly 5, which is adapted for use with a cervical spine-locking bone plate having a plurality of fastener holes. While the surgical drill-guide assembly is described in conjunction with a cervical locking plate it will be appreciated that the reference to a cervical locking plate is only exemplary, and that the surgical drill-guide assembly can be used with a variety of bone plates, including a locking and a nonlocking bone-plate as well as for example, bone plates for long bones, maxillofacial applications, etc.

The drill-guide assembly 5 can be secured or locked into a fastener hole in a bone plate. Locking or securing may facilitate precision in the surgical procedure, for example, drilling or fastening screws or other similar fasteners. Moreover, the drill-guide can be quickly detached and released from the bone-plate improving the speed of surgical procedures involving drilling or similar procedures.

Drill-guide assembly 5 includes an alignment assembly 15, a release knob 100, a handle member 250, a ratchet-gear mechanism 50, and a dual-arm support 10.

The alignment assembly 15 comprises an alignment drill-barrel 150 and a bushing 200. A surgeon or a user can releasably attach the alignment assembly 15 in the fastener hole 352 of a bone-plate 350. A drill-bit or other such instrument can be inserted into and through the alignment assembly 15.

Figure 2:
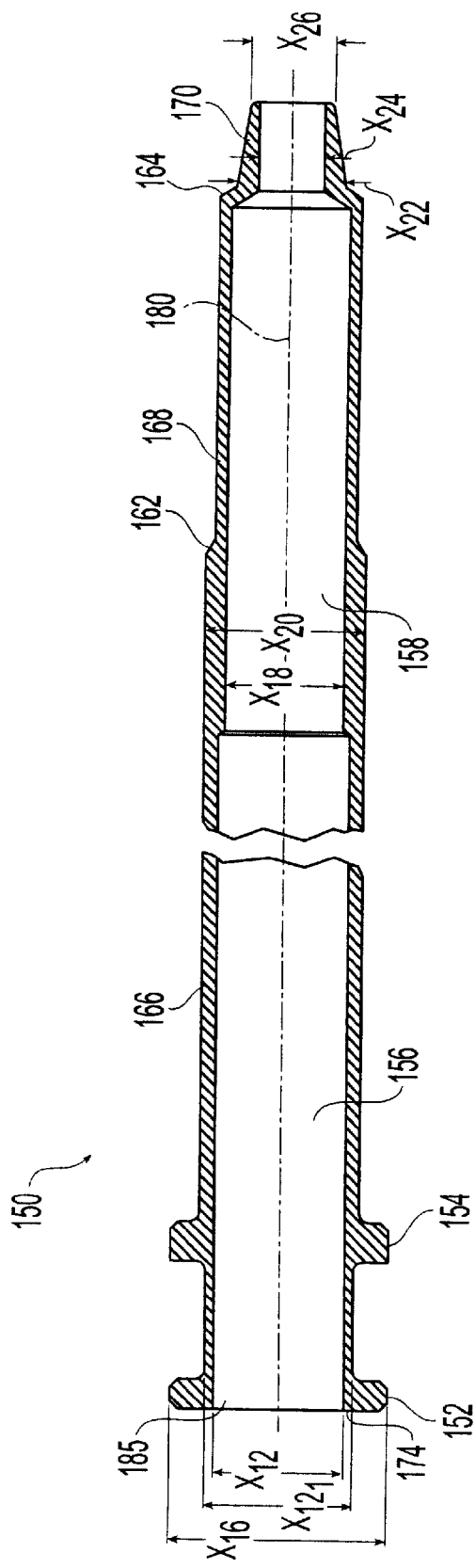
FIG. 2 is a cross-sectional view of the alignment drill-barrel in accordance with a preferred embodiment of the present invention.

Referring to FIG. 2, a preferred embodiment of the alignment drill-barrel 150 is shown. The alignment drill-barrel 150 preferably has a through bore 185 from its proximal end 174 to its distal end 172. A drill-bit or other instrument may be inserted through the bore 185. In the embodiment of FIG. 2 the drill-barrel comprises a first hollow cylindrical section 156 with an annular diameter of $x_{12}$, a second hollow cylindrical section 158 with an inside annular diameter of $x_{18}$, and a third hollow cylindrical section 160 with an inside annular diameter of $x_{24}$, wherein $x_{24}$ is smaller than $x_{18}$, and $x_{18}$ is smaller than $x_{12}$. The outside surface of the alignment drill-barrel 150 comprises a shoulder 162 and a shoulder 164 wherein the outside diameter of the first section 166 is $x_{14}$ which is greater than the outside diameter $x_{20}$ of the second section 168. $x_{14}$ has an exemplary diameter of 3 mm to 10 mm, preferably about 8 mm. The third section 170 is a conical section that tapers from an outside diameter $x_{22}$ at shoulder 164 to a diameter $x_{26}$ at the distal end 172. The proximal end 174 of the alignment drill-barrel 150 preferably has first circular ridge 152 and second circular ridge 154. The first and the second circular ridges 152 and 154 respectively, have an outside diameter $x_{16}$.

In a preferred embodiment the first circular ridge 152 is flush with the proximal end 174 of the alignment drill-barrel 150. The conical section 170 tapers from an outside diameter $x_{22}$ at the transition 164 to an outside diameter $x_{26}$ at end 172. Preferably, inner diameter $x_{24}$ is constant along the length of conical section 170 of alignment drill-barrel 150 as defined along center line 180.

Figure 3:
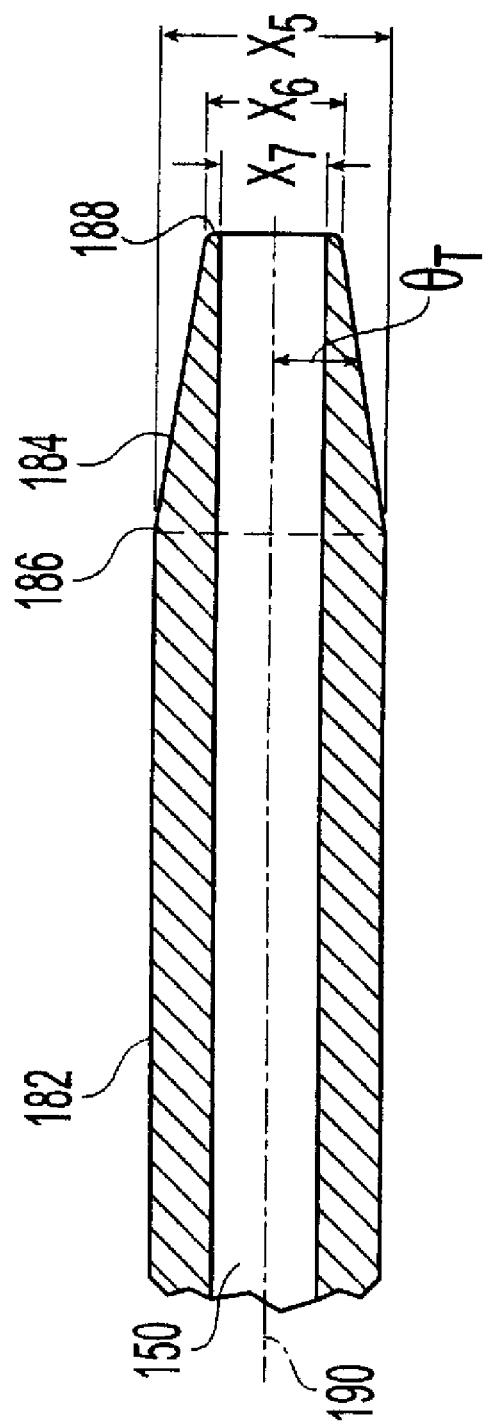
FIG. 3 is a partial cross-sectional view of the alignment drill-barrel in accordance with another preferred embodiment of the present invention.

Referring to FIG. 3, an alignment drill-barrel 150 according to another embodiment is shown. In FIG. 3, alignment drill-barrel 150 is hollow with a cylindrical section 182 and a tapered, conical section 184 to facilitate movement of alignment drill-barrel 150 within bushing 200. Cylindrical section 182 has outside diameter $x_5$, while conical section 184 tapers from an outside diameter $x_5$ at the transition 186 to an outside diameter $x_6$ at the distal end 188. Preferably, inner diameter $x_7$ is constant along the length of alignment drill-barrel 150 as defined along center line 190.

Figure 4:
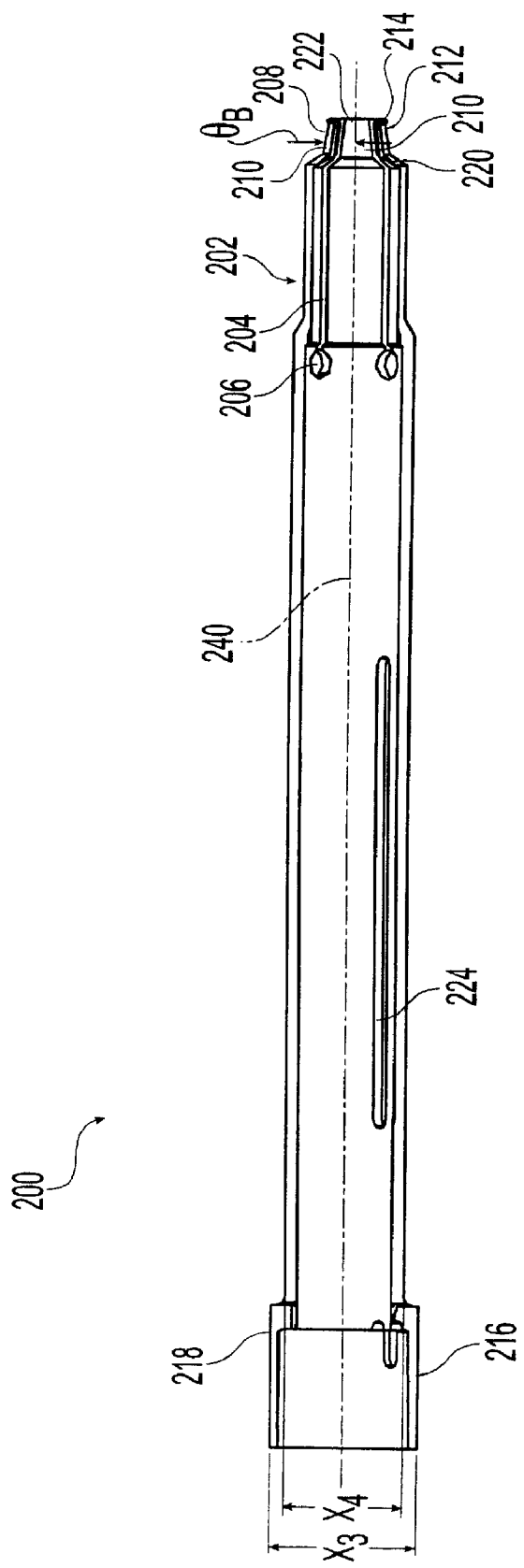
FIG. 4 is a cross-sectional view of an embodiment of the bushing.

Referring to FIG. 4, a preferred bushing is shown. Bushing 200 coaxially receives alignment drill-barrel 150 about a central line 240. Preferably, bushing 200 is substantially symmetrical about line 240. The forward end 222 of bushing 200 is preferably comprised of longitudinally extending fingers 210. Individual fingers 210 are separated by slits 204 extending longitudinally between adjacent fingers 210. Slits 204 as shown, for example, in FIG. 4, may include a circular portion 206 that serves to minimize stress concentration when fingers 210 are flexed. Fingers 210 are resiliently biased inwardly and naturally assume an inward disposition when in a relaxed state. At a front portion of the expandable forward end 202 of bushing 200, the fingers 210 form a radially expandable circumferential neck 208. At the back end of and adjacent to neck 208 is preferably a shoulder 212.

Preferably, neck 208 spans a length that is slightly longer than the thickness of the fastener hole wall from the bone-side surface to the top surface of a bone-plate. Thus, neck 208 can be inserted into the bone-plate fastener hole 352 and the fingers 210 expanded to secure the bushing 200 to the plate. More particularly, movement of alignment drill-barrel 150 within bushing 200 expands fingers 210 to secure the bushing 200 to the bone plate. In this manner, the drill-guide assembly can be secured to the plate, restricting relative movement. In a preferred embodiment, fingers 210 forming a radially expandable rim 214 are provided at the front end of and adjacent to neck 208.

In another embodiment, the distal end 222 of the bushing 200 may not contain the rim 214, the neck 208 or the shoulder 212, but instead has a tapered end with the inner and the outer diameter of the tapered end decreasing from point 220 shown in FIG. 4. In a preferred embodiment, the taper is such that it fits freely through a fastener hole in a bone plate.

In alternate embodiments, no rim may be used. The several portions of bushing 200, i.e., the neck 208, the shoulder 212, and the rim 214, are preferably a single piece of material of unitary construction.

In other alternate embodiments, fingers 210 need not include a shoulder, neck, and/or a rim. Instead, for example, a small pin may be used to secure the bushing to the plate. In an alternatively preferred embodiment, the inward bias of fingers 210 is selected to produce the desired friction with the bone-plate 350 so that the fingers 210 fit snugly within the bone-plate fastener hole 352, preferably allowing operation of handle member 250 with only one hand. Alternative resiliency for fingers 210 may be varied to suit the purpose of the design.

In a preferred embodiment bushing 200 has one or more longitudinal slots on its side 224 in axial direction 240 just above the circular portion 206. These slots provide better cleaning during autoclave or other disinfection and/or cleaning procedures.

Referring to FIG. 4, bushing 200 has a circumferential ridge 218 with an outer diameter $x_3$, and a region 216 has an outer diameter $x_4$. $x_4$ has an exemplary dimension of 4 mm to 20 mm, preferably about 8 mm.

Figure 5:
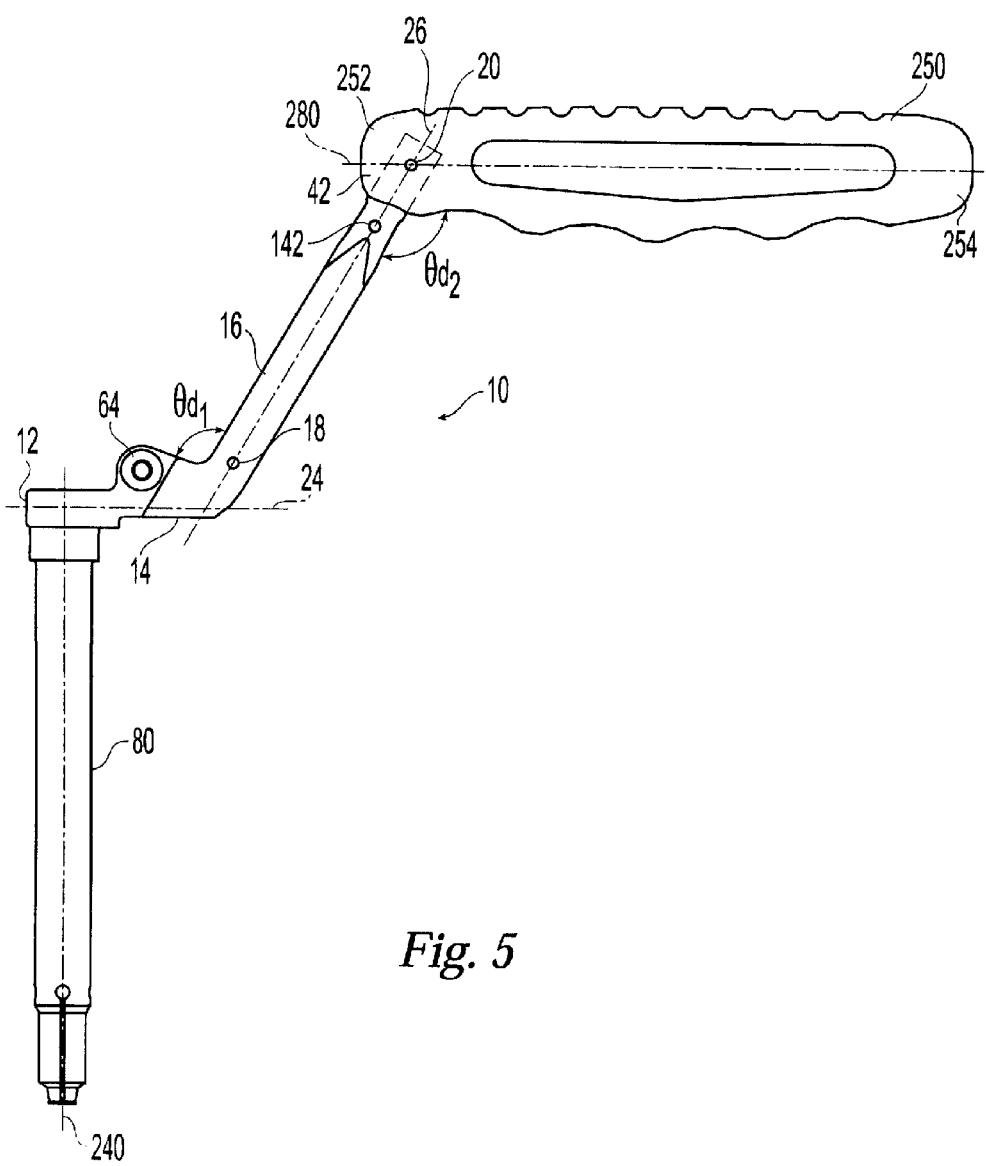
FIG. 5 is a side view of the dual-arm support attached to the bushing and handle member.

As shown in FIG. 5, in one embodiment, dual-arm support 10 connects the handle member 250 to the alignment assembly 15. More specifically, in the exemplary embodiments of FIGS. 1 and 2, the dual-arm support 10 is fixedly connected at its end to the proximal end 174 of the alignment assembly 15. Dual-arm support 10 preferably is generally "L-shaped" with first part 14 connected to bushing 200. More specifically, end 12 of dual-arm support 10 is attached to ridge 218 at the proximal end 242 of the bushing 200.

The dual-arm support 10 is preferably fixed with the bushing 200 by welding. In an alternative embodiment, friction fitting, press fitting, and such can be used. Outer diameter $x_3$ of ridge 218 is about the same size as inner diameter $x_1$ of the clamp 12 of the dual-arm support 10. Bushing 200 may also be fixed to dual-arm support 10 by releasable fastener means. First part 14 is generally perpendicular to the axial direction of the alignment assembly 15 or the bushing 200. The second part 16 of the dual-arm support 10 preferably forms an obtuse angle $\theta_{d1}$ with the first part 14 of the dual-arm support 10. $\theta_{d1}$ may range from about 90° to about 180°, and more preferably from about 105° to about 135°. Dual-arm support 10 and handle member 250 are fixedly connected by a dowel pin 20 at the front end of the handle member 250, so that they are immovable with respect to each other. In the preferred embodiment, handle member 250 is located remotely from the drilling site, thereby increasing visibility near the locking bone plate 350.

As shown in FIG. 5, the second part 16 of the dual-arm support 10 may be attached to the first part 14 by a dowel pin 18, or the dual-arm support 10 may be an integral, monolithic construction. The second part 16 of the dual-arm support 10 also forms an obtuse angle $\theta_{d2}$ with the handle member 250. $\theta_{d2}$ may range from about 90° to about 180°, and more preferably from about 105° to about 135°. The handle member 250 and the dual-arm support 10 generally form an "S" shape or a zigzag shape, and in a preferred embodiment, the longitudinal axis 24 of the first part 14 and the longitudinal axis 26 of the second part 16 lie in the same plane. The longitudinal axis 280 of the handle member 250 also preferably lies in the same plane as the longitudinal axis 24 of the first part 14 and the longitudinal axis 26 of the second part 16 of the dual-arm support 10. Preferably the longitudinal axis 24 of the first-part 14 of the dual-arm support 10 is generally parallel with the longitudinal axis 280 of the handle member 250.

Figure 6:
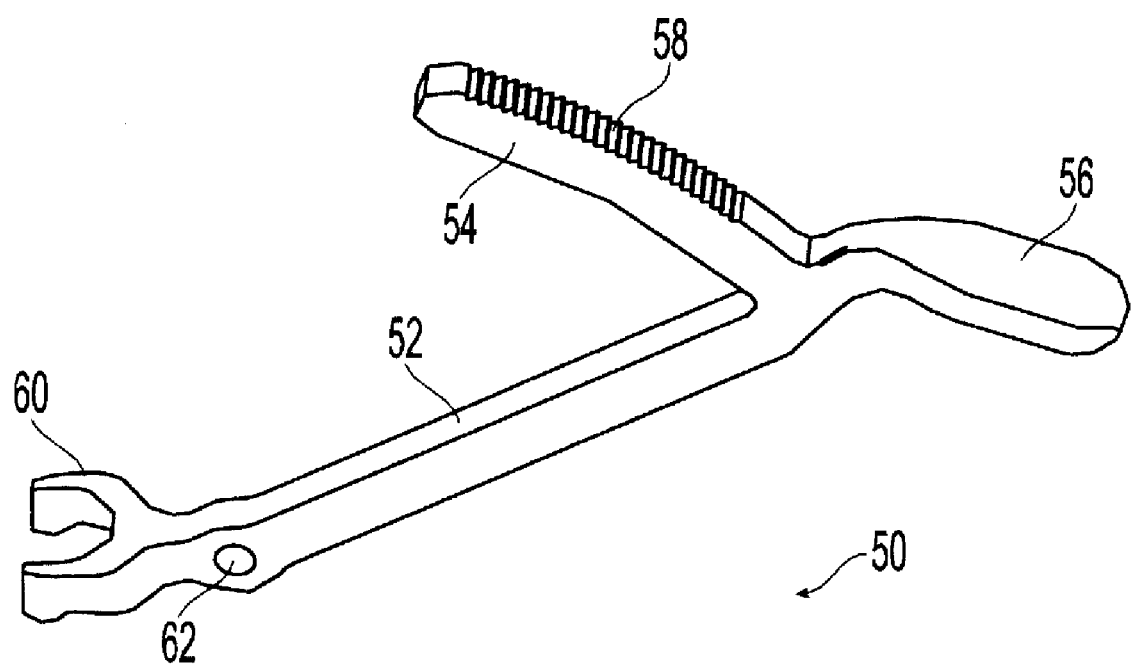
FIG. 6 is a perspective view of the Y-shaped ratchet-gear mechanism.

Referring to FIG. 6, there is shown an exemplary embodiment of the ratchet-gear mechanism 50. The ratchet-gear mechanism 50 allows the user to manipulate the locking and release of the drill-guide assembly 5 with the bone-plate 350 by engagement and disengagement, respectively, of the pawls 58 with the serrations 102. The ratchet-gear mechanism 50, in a preferred embodiment is generally "Y-shaped" with a first leg 52, a second leg 54, and a tail 56.

Figure 6A:
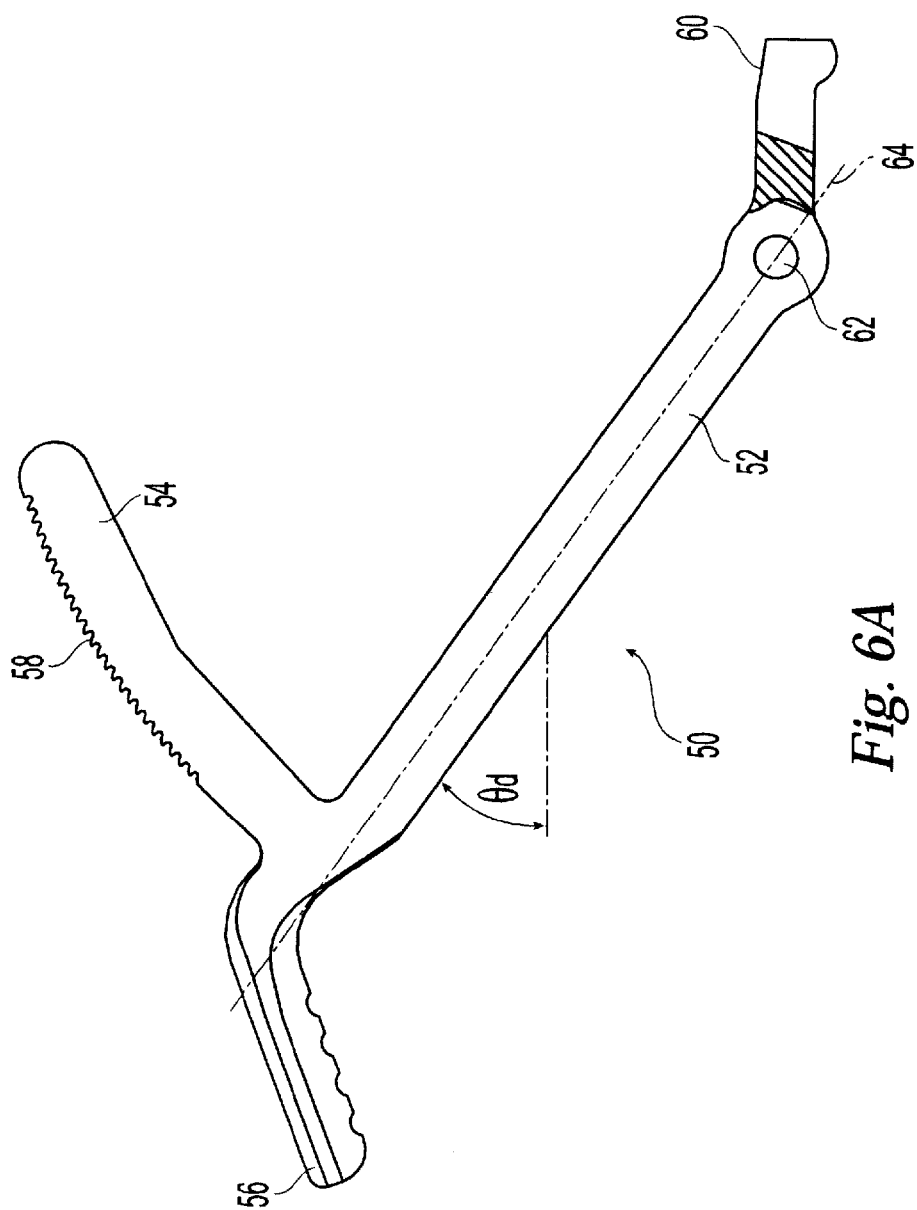
FIG. 6a is a side view of the Y-shaped ratchet-gear mechanism.
Figure 6B:
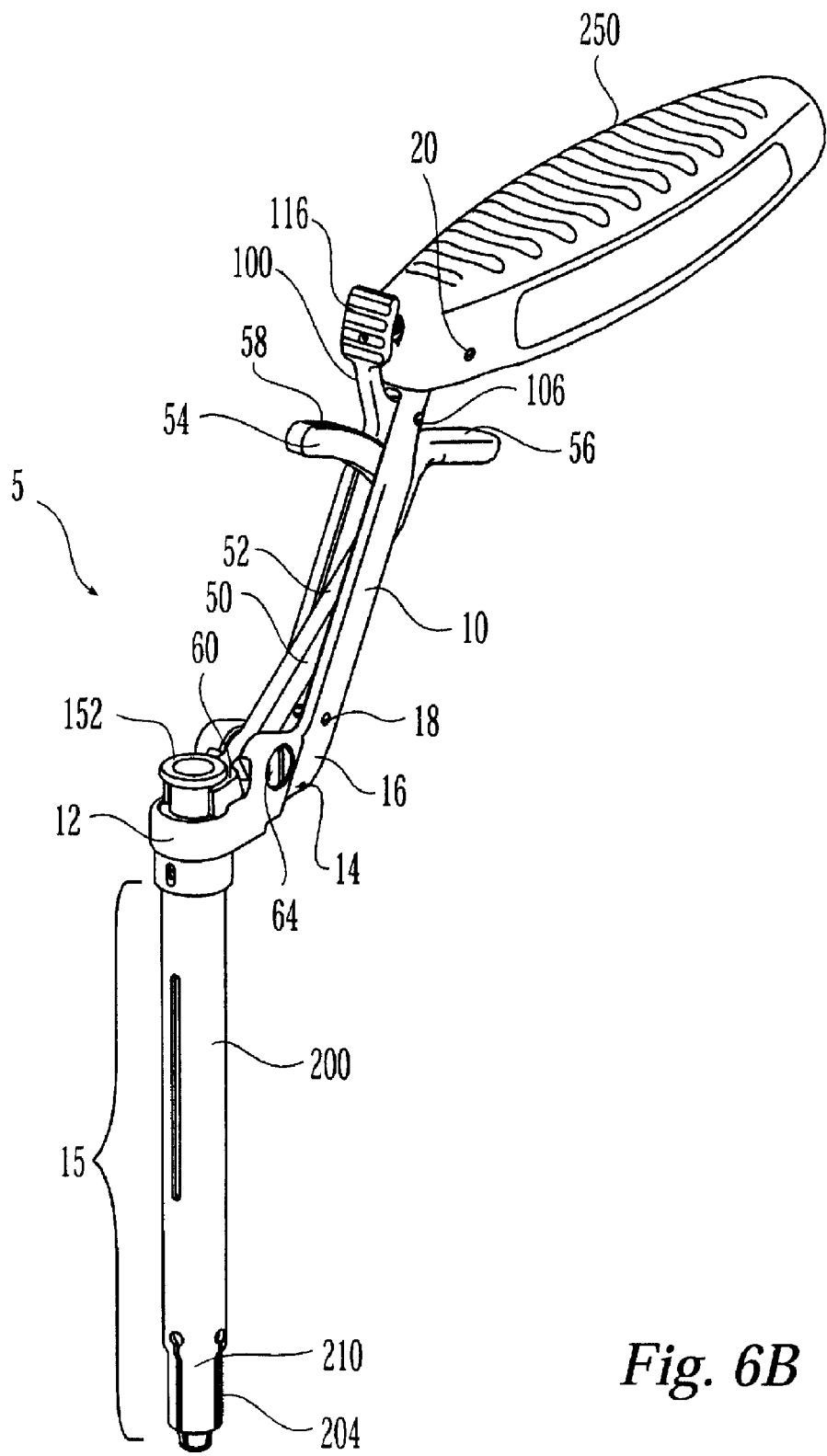
FIG. 6b is a perspective view of the drill-guide assembly showing the ratchet-gear mechanism connected to the dual-arm support.

The first leg 52 of the ratchet-gear mechanism comprises a generally C-shaped vice-grip 60 at its end, and a pivot hole 62 for insertion of a pivot screw 64. The C-shaped vice-grip 60 grips the alignment drill-barrel 150 in between the first ridge 152 and second ridge 154 (see also FIG. 2) located at the end 174 of the drill-barrel 150. As shown in FIG. 6a, in a preferred embodiment, the plane of the C-shaped vice-grip 60 that forms an anterior portion of the first leg 52 of the Y-shaped ratchet-gear mechanism 50 makes an acute angle $\theta_d$ with the longitudinal axis 64 of the first leg 52 of the Y-shaped ratchet-gear mechanism 50. At the point of inflexion between the longitudinal first leg 52 and the C-shaped vice grip 60, pivot screw 64 and hole 62 are located. This pivot mechanism 62 helps the movement of the alignment drill-barrel 150. In a preferred embodiment, the acute angle is from about 25° to about 45°. In a further preferred embodiment the acute angle $\theta_d$ is such that when the ratchet-gear mechanism 50 is completely disengaged from the serrations 102 of the release knob 100, the alignment drill-barrel 150 can be removed from the bushing 200 in a longitudinal direction away from the fingers 210 by moving the ratchet-gear mechanism 50 in a direction away from the handle member 250, about the pivot screw 64. $\theta_d$ may be 0° to 90°, with an exemplary dimension of 60°.

The second leg 54 of the Y-shaped ratchet-gear mechanism 50 comprises horizontal pawls 58 which engage serrations 102 at the end of the release knob 100. The tail 56 of the Y-shaped ratchet-gear mechanism 50 acts as a trigger for a user to apply a force to actuate movement of the alignment drill-barrel 150.

Figure 7:
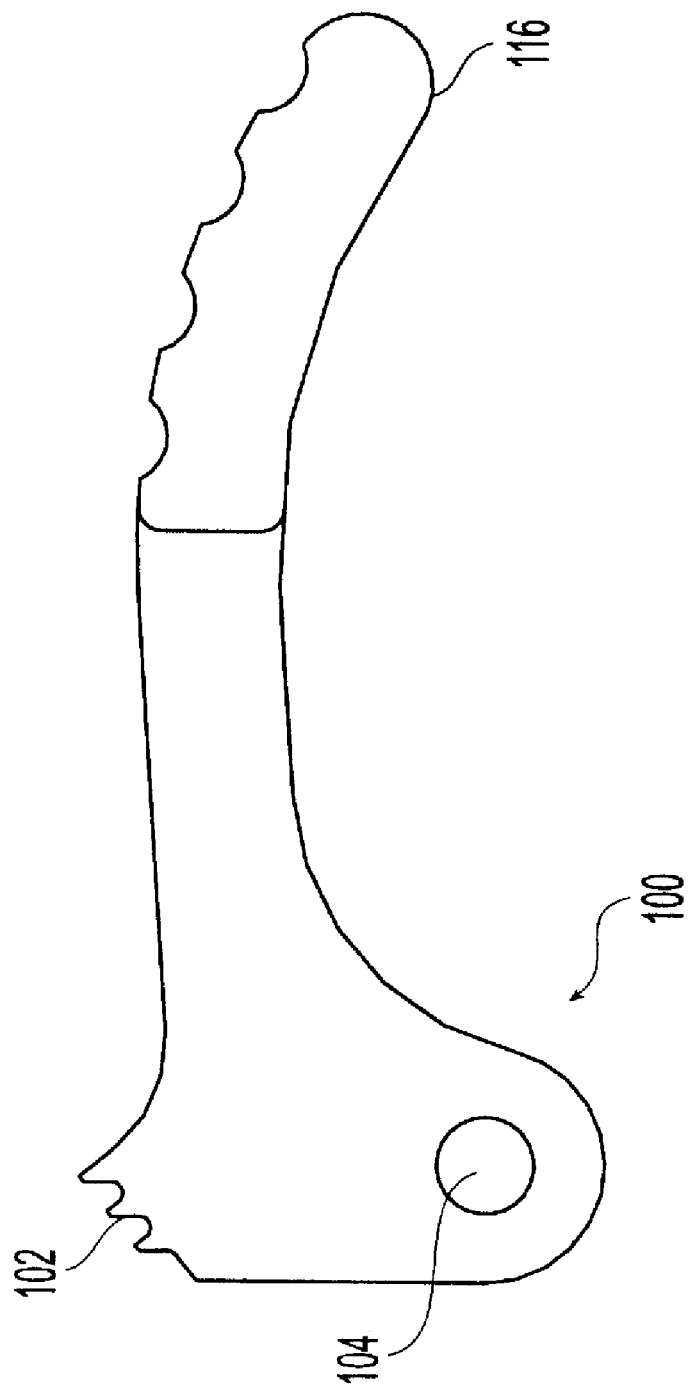
FIG. 7 is a side view of the release knob.
Figure 7A:
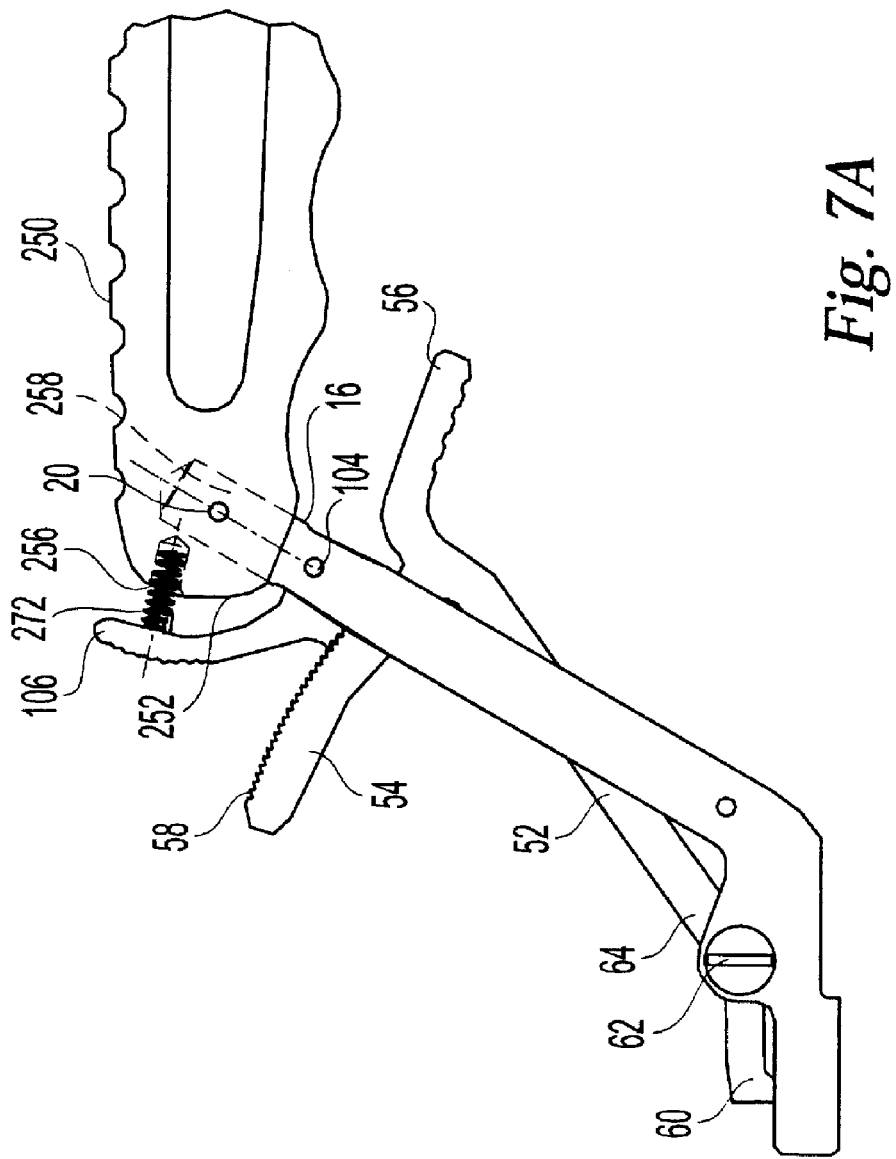
FIG. 7a is a perspective view of the ratchet-gear mechanism engaging the release knob.

Referring to FIG. 7, the release knob 100 is pivoted about a dowel pin 106 which is inserted through the dowel pin hole 104 in the release knob 100, and the release knob hole 142 in the second part 16 of the dual-arm support 10. With pivotal support from the dowel pin 106, the serrations 102 on the surface of the release knob 100 can engage with the pawls 58 on the second leg 54 of the Y-shaped ratchet-gear mechanism, when the tail 56 (trigger) of the Y-shaped ratchet-mechanism is pressed or moved in a direction toward the handle member 250. In a preferred embodiment, the release knob 100 has a rubber sleeve 106 or a sleeve made from a material which provides a firm traction when the surgeon or the user presses the release knob 100. Alternatively, or additionally the surface of the release knob may have surface texturing to increase the traction when a surgeon or a user manipulates the release knob 100.

Figure 8:
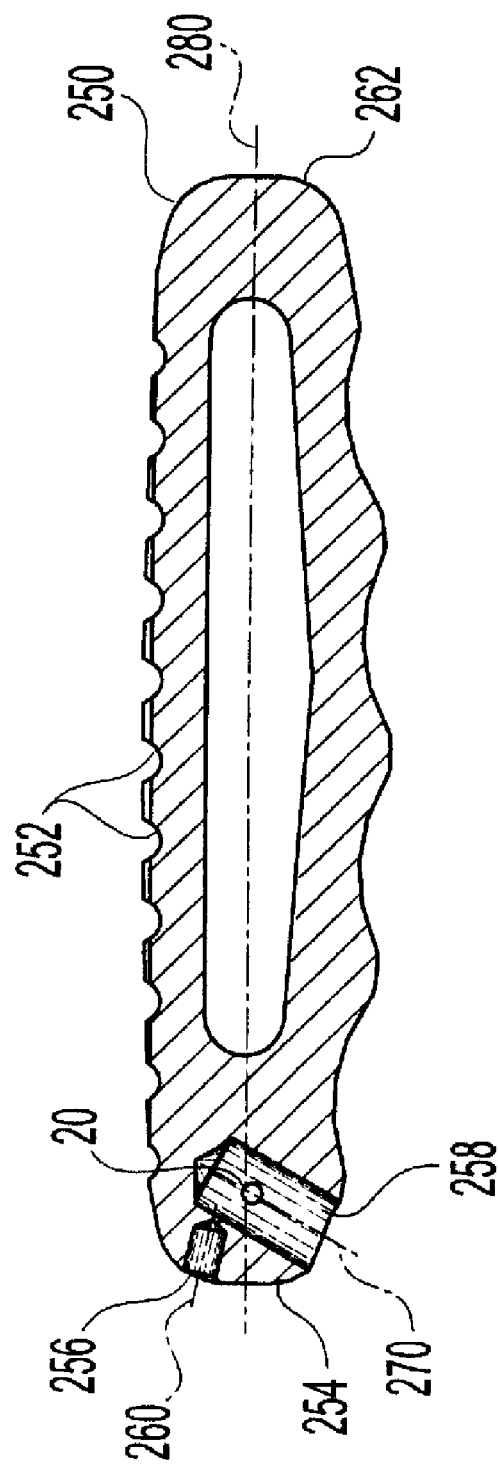
FIG. 8 is a side view of the handle member of the drill-guide assembly.

Referring to FIG. 8, handle member 250 is shown. Handle member 250 is generally oval shaped with broad grooves 252 on top to provide better grip to the surgeon or user when using the drill-guide assembly 5. At the front end 254 of the handle member 250, there are two cavities, the first cavity 256 and the second cavity 258. The first cavity 256 has an axis along line 260 and the second cavity 258 has an axis along line 270. The first cavity 256 houses compression spring 272 and the second cavity 258 houses the dual-arm support 10, or more specifically the second part 16 of the dual-arm support 10. The second part 16 of the dual-arm support 10 is fixed to the handle member 250 by a dowel pin 20. The dowel pin 20, in a preferred embodiment, is generally perpendicular to the axis 280 of the handle member 250. Exemplary dimensions of the handle are 100 to 150 mm long with a width at the widest point of 15 mm to 40 mm.

When a surgeon or a user presses the trigger 56, toward handle member 250, the ratchet-gear mechanism 50 swivels. Due to the movement of the Y-shaped ratchet-gear mechanism 50 in the direction of the handle member 250, the alignment drill-barrel 150 moves the bushing 200 in the downward direction toward the bone-plate 350. Due to the conical shape 170 of the alignment drill-barrel 150 (FIG. 2), the fingers 210 on the bushing 200 expand in an outward direction as the front end 172 of alignment drill-barrel 150 approaches the front edge 214 of bushing 200. When the outward diameter of the fingers 210 matches that of the fastener hole 352, the drill-guide assembly 5 locks to the bone-plate 350. A surgical drill-bit 400 or any other appropriate bit, screw, tap, awl, or such device, can be inserted through the alignment drill-barrel 150.

Alignment drill-barrel 150 is configured and dimensioned to be slidably received within bushing 200. The alignment drill-barrel 150 and bushing 200 cooperate to permit drill-guide assembly 5 to lock to a bone plate 350. The conical section 184 of the alignment drill-barrel 150 cooperates with fingers 210 of bushing 200 to expand fingers 210 when the alignment drill-barrel 150 is moved into a locked position. The conical section 184 of alignment drill-barrel 150 pushes outwardly against the inner surface of the bushing 200 as alignment drill-barrel 150 is moved forward to expand the forward end 214 of the bushing 200. In this embodiment, the conical section mates with and pushes against the inner surface of the bushing 200 forward of circular portion 206 of slits 204 in fingers 210, to push the fingers 210 radially outward (See FIG. 4).

Alignment drill-barrel 150 is aligned within bushing 200, such that center line 240 or 190 is collinear with line 180. Preferably, when bushing 200 is placed in a fastener hole of a bone plate, and ratchet-gear mechanism 50 is actuated such that the almost fully actuated position is reached (i.e. when trigger 56 is substantially parallel to handle member 250), end 172 of alignment drill-barrel 150 is substantially coplanar with rim 214 of bushing 200. It should be noted that alignment drill-barrel 150 is coaxially received in bushing 200 which is also the path of surgical drill-bit 400 inserted in cannula 182 of the alignment drill-barrel 150.

Generally, a surgeon or user must continue to depress the trigger 56 and handle member 250 toward each other to maintain an actuated position of Y-shaped ratchet-gear mechanism. Depending on the size of the fastener hole 352 and the firmness of the locking desired, the pawls 58 located on the second leg 54 of the Y-shaped ratchet-gear mechanism 50 engage with the serrations 102 on the release knob 100 holding the ratchet-gear mechanism 50 in place. The release knob 100 preferably is held firm in its position by the compression force of the spring mechanism 272, which is located at the front end 254 inside the cavity 256 of the handle member 250. With the ratchet-gear mechanism 50 provided in this drill-guide assembly 5, the serrations 102 on the release knob 100 can be used to releasably lock Y-shaped ratchet-gear mechanism 50 at the desired level of actuation. This obviates the need for a surgeon or user to continue to depress the trigger 56 relative to handle member 250 after desired actuation has occurred. The pawls 58 on the second leg 54 of the Y-shaped ratchet-gear mechanism 50 engage the serrations 102 on the release knob 100 when the trigger 56 is pressed sufficiently. The release knob 100 is held in a fixed position as a result of the compression force exerted by the compressed spring 272.

When the release knob 100 is pressed in the direction of the front end 254 of the handle member 250, the spring member 272 is compressed, the pawls 58 are disengaged from the serrations 102, and the Y-shaped ratchet-gear mechanism 50 becomes unactuated. When the Y-shaped ratchet-gear mechanism 50 is unactuated, the force that is keeping the alignment drill-barrel 150 in a position toward fingers 210 is released. As a result, the alignment drill-barrel 100 is no longer pushing the fingers 210 on the bushing 200 in an outward direction toward the bone-plate 350. The alignment drill-barrel 150 can be then moved in a longitudinal direction away from the fingers 210 on the bushing 200. As a result, the bushing 200 assumes a retracted position as demonstrated in FIG. 9. Once the fingers 210 retract, the drill-assembly 5 unlocks from the fastener hole 352 of the bone-plate 350 and the user or surgeon can withdraw it.

When the release knob 100 is pressed to further compress the spring, the pawls 58 disengage from serrations 102, thereby de-actuating the Y-shaped ratchet-gear mechanism 50, which in turn, through the pivot action at the pivot screw 64 results in the movement of the alignment drill-barrel 150 in a direction away from the bone-plate 350.

Advantageously, a surgeon or user can operate drill-guide 5 with only one hand, due to the ergonomic positioning of trigger 56 and handle member 250. With the embodiment illustrated in FIG. 1, a user can attach the drill-guide by using a finger, such as an index finger, to engage and manipulate the tail 56 of the ratchet-gear mechanism 50, and while a second different finger, such as a thumb, to engage and manipulate the release knob 100.

Figure 9:
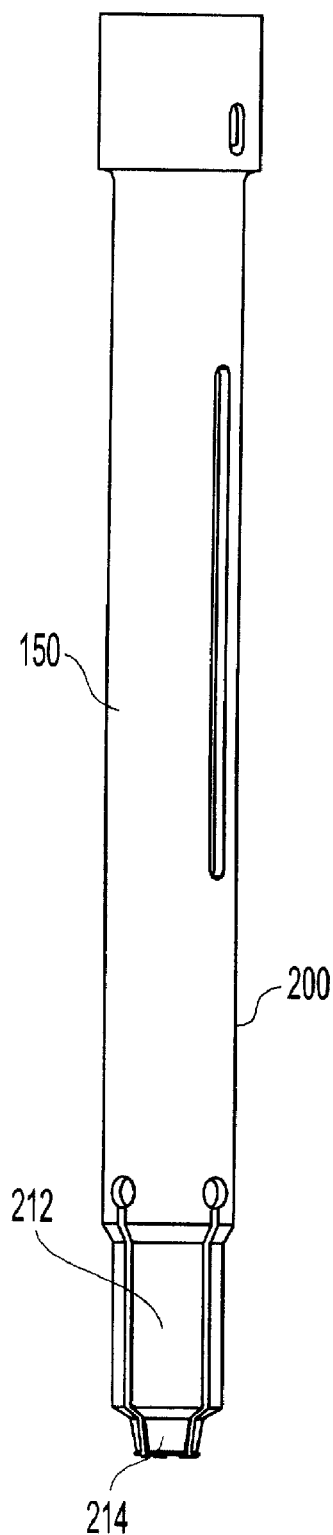
FIG. 9 is a side view of the bushing with fingers in retracted position.
Figure 10:
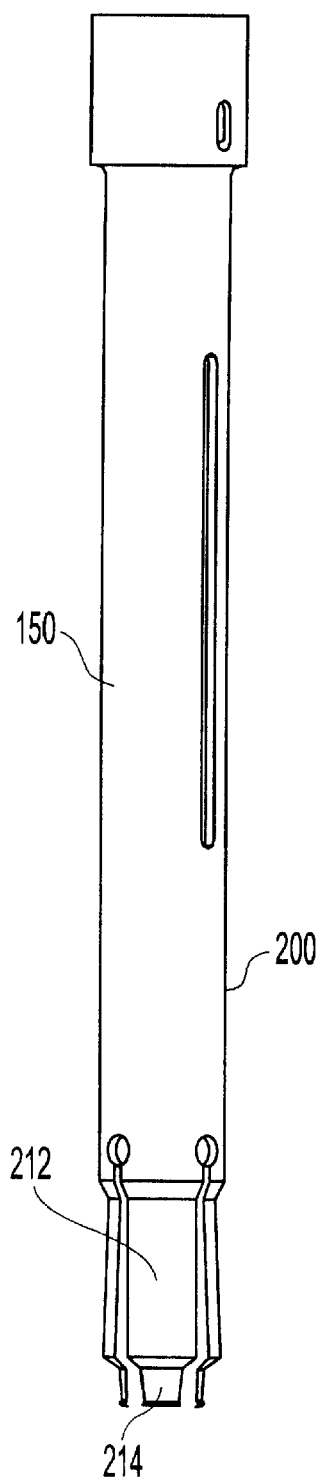
FIG. 10 is a side view of the bushing with fingers in expanded position.

When the alignment drill-barrel 150 is in the unlocked position as shown in FIG. 9, the conical section 184 allows fingers 210 to return to a relaxed, contracted position. This allows bushing 200 to be inserted and retracted from plate fastener hole. The inner surface of the bushing 200 forward of steps 220 in bushing 200 is preferably tapered at an angle $\theta_B$ to line 240 that is about 1 degree more than taper angle $\theta_T$ of conical sections 184, and preferably angle $\theta_B$ is about 4 degrees. A desirable amount of movement of alignment drill-barrel 150 within bushing 200 is thus provided to bias fingers 210 of bushing 200 from a contracted position to an expanded position. Alternative taper angles of conical section 184 and inner surface of bushing 200 may be chosen according to varying design criteria. In addition, a preferred, short movement of trigger 56 (ratchet-gear mechanism 50) is required to expand and contract fingers 210 of bushing 200.

Before and during bone plate implantation, the surgeon or user may insert the expandable distal end 222 of bushing 200 in particular neck 208 and rim 214, into fastener hole 352 in a bone plate 350. By pressing trigger 56 of the Y-shaped ratchet-gear mechanism 50 relative to the handle member 250, the surgeon or user may grasp and manipulate the plate 350 without an additional plate holder if so desired. Preferably, friction between the forward conical section 184 of the alignment drill-barrel 150 and the inner surface of fingers 210 especially at neck 208 and rim 214 retains the expandable distal end 222 of bushing 200 in an expanded, locked position. Thus, when bushing 200 is in the expanded, locked position in a fastener hole of a plate placed in position for implantation, movement of the plate during the drilling operation can be minimized.

Drill-barrel 150 is preferably sized so that once the bone plate 350 is properly positioned over the implantation site and bushing 206 is locked to the plate, the insertion point of a surgical drill-bit 400 at the proximal end of drill-barrel 150, is located at a distance beyond the patient's body such that a spinning surgical drill-bit 400 will not laterally reach or harm surrounding tissues that the surgeon or user does not intend to drill.

Preferably, the surgical drill-bits used with surgical drill-guide assembly 5 are configured and dimensioned to drill holes of about 12, 14, or 16 mm in depth. Suitable drill-bits typically have integral stops so that when the drill-bits are used with alignment drill-barrel of an established length, the holes produced by the drill-bit will not be deeper than the intended depth using a given bit. The stops may be positioned to abut the upper surfaces at the proximal end of drill-barrel 150, when a drill-bit has been inserted in the barrel to a particular depth.

Those skilled in the art will recognize that bushing 200 may be configured and dimensioned to fit bone plate fastener holes with shapes other than circular. For example, bushing 200 may be adapted to fit elliptical, hexagonal, star-shaped, or square fastener holes.

Preferably, the components of surgical drill-guide assembly 5 are metallic, passivated, and electropolished. Most preferably, the components are formed of stainless steel, except for the springs which are formed of spring steel, although other materials may be used. Preferably, at least the handle member is forged, while the other components may be machined, and the surgical drill-guide assembly preferably has a matte finish so that the surfaces of the components do not reflect operating room light in such a manner as to distract the surgeon or user. Some components may be subjected to heat treatments so that the surfaces are work hardened. The surfaces are preferably burr-free. Preferably, the surface finish allows individual components to move with respect to each other in a smooth and non-binding fashion through each component's entire range of motion. Additionally, all pins and fasteners are preferably flush with the surfaces into which they are fixed.

Figure 11:
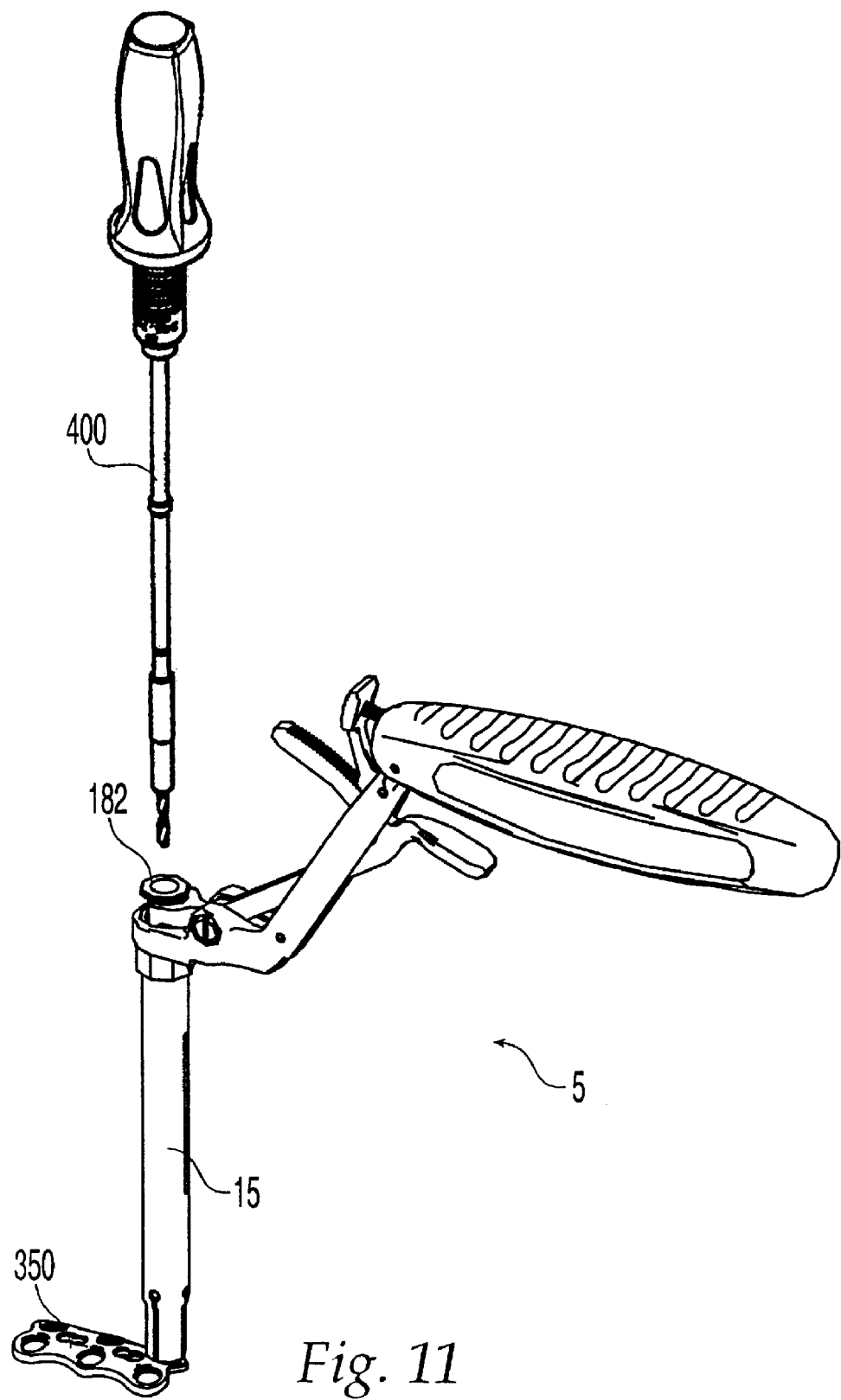
FIG. 11 is a perspective view of the drill-guide assembly locked to a bone-plate.

The present invention also involves a method of drilling holes. A surgeon or user inserts the bushing of a surgical drill-guide assembly into fastener holes of a bone-plate and depresses the ratchet-gear mechanism to slide the alignment drill-barrel forward, expanding the bushing preferably by the conical portions of the alignment drill-barrel radially spreading the fingers in the bushing. The surgeon or user then locks the bushing to the plate by locking the alignment drill-barrel and the bushing in fixed relation to each other, thereby relieving the surgeon or user of the need to squeeze the ratchet-gear mechanism toward the handle (See FIG. 11). The surgeon or user aligns the surgical drill-bit along the drilling axis defined through the center of the bore in the alignment drill-barrel and inserts the drill-bit in the barrel. The surgeon or user then drills a first hole coaxial with the central axis of a first fastener hole in the plate. The drill-bit is stopped at a predetermined distance to provide a hole of predetermined depth. The drill-bit is removed from the alignment drill-barrel. The bushing is thereafter unlocked from the plate by pressing the release knob, which releases the bushing from the fastener hole so that the user can then freely and unfetteredly remove the drill-guide assembly from the plate.

While the invention has been shown and described herein with reference to particular embodiments, it is to be understood that the various additions, substitutions, or modifications of form, structure, arrangement, proportions, materials, and components and otherwise, used in the practice of the invention and which are particularly adapted to specific environments and operative requirements, may be made to the described embodiments without departing from the spirit and scope of the present invention. For example, the surgical drill-guide assembly may have alignment drill-barrel that can be angulated in the cephalad/caudal or sagittal planes, thereby permitting a range of angles to be chosen for the holes to be drilled and further permitting a range of spacings of plate holes to be accommodated. Moreover, alignment drill-barrel that is removeably attachable to the base may be provided so that a surgeon or user may select alignment drill-barrel with holes that precisely accommodate a desired drill-bit size. In addition, the drill-guide assembly handle may include a grip that generally follows the contours of fingers that hold the grip. The presently disclosed embodiments are therefore to be considered in all respects as illustrative and not restrictive, the scope of the invention being indicated by the appended claims, and not limited to the foregoing description.

What is claimed is:

1. A drill-guide assembly, comprising:
   an alignment drill-barrel configured to receive and guide a drill-bit, the alignment drill-barrel having a proximal end and a distal end;
   a bushing configured to slidably receive the alignment drill-barrel, the bushing having a radially expandable forward-end and a proximal end, the forward-end configured to be insertable within a fastener hole in a bone plate;
   a release knob having serrations; and
   a movable ratchet gear mechanism having a first leg, a second leg and a tail,
   the first leg of the ratchet-gear mechanism connected to the alignment drill-barrel,
   the second leg of the ratchet-gear mechanism having pawls configured and adapted to engage the serrations to hold the alignment drill-barrel in position,
   the tail of the ratchet gear mechanism operable by a user to selectively move the ratchet-gear mechanism,
   wherein, movement of the ratchet-gear mechanism slides the alignment drill-barrel relative to the bushing to radially expand the forward end to releasably lock the bushing to the plate.

2. The drill-guide assembly, as recited in claim 1, wherein the ratchet-gear mechanism is pivotably mounted.

3. The drill-guide assembly, as recited in claim 1, wherein the release knob is pivotably mounted.

4. The drill-guide assembly, as recited in claim 1, wherein the ratchet-gear mechanism swivels incrementally.

5. The drill-guide assembly, as recited in claim 1, wherein the alignment drill-barrel comprises a through bore from the distal end to the proximal end.

6. The drill-guide assembly, as recited in claim 1, wherein the alignment drill barrel further comprises a first hollow cylindrical section, a second hollow cylindrical section and a third hollow cylindrical section wherein the annular diameter of the third cylindrical section is at least equal to the annular diameter of the second cylindrical section, and wherein the annular diameter of the second cylindrical section is at least equal to the annular diameter of the first cylindrical section.

7. The drill-guide assembly, as recited in claim 1, wherein the annular diameter of the third cylindrical section is constant along the center line of the cylindrical section.

8. The drill-guide assembly as recited in claim 1, wherein the alignment drill-barrel further comprises two ridges at the proximal end.

9. The drill-guide assembly, as recited in claim 8, wherein the outside surface of the alignment drill barrel has a shoulder at the distal end.

10. The drill-guide assembly, as recited in claim 8, wherein the outside diameter of the third cylindrical section tapers to form a conical shape.

11. The drill-guide assembly, as recited in claim 1, wherein the bushing further comprises radially expandable fingers.

12. The drill-guide assembly, as recited in claim 11, wherein the fingers form a radially expandable circumferential neck and assume an inward unexpanded disposition in relaxed state.

13. The drill-guide assembly, as recited in claim 12, wherein the bushing further comprises a shoulder adjacent to the radially expandable circumferential neck.

14. The drill-guide assembly, as recited in claim 11, wherein the distal end of the bushing comprises a tapered end with the inner and the outer diameter of the tapered end decreasing in direction of the tip.

15. The drill-guide assembly, as recited in claim 11, wherein the bushing is made from a single piece of material of unitary construction.

16. The drill-guide assembly, as recited in claim 11, wherein the bushing further comprises a pin for securing the drill-guide assembly to a bone-plate.

17. The drill-guide assembly, as recited in claim 11, wherein the bushing comprises of at least one vertical slot above a circular portion on the bushing.

18. A drill-guide assembly comprising:
an alignment drill-barrel configured to receive and guide a drill-bit, the alignment drill-barrel having a proximal end and a distal end;
a bushing configured to slidably receive the alignment drill-barrel, the bushing having a radially expandable forward-end and a proximal end, the forward-end configured to be insertable within a fastener hole in a bone plate;
a handle member for grasping by a user;
a dual-arm support having first and second parts, the first part of the dual-arm support fixedly connected to the proximal end of the bushing and the second part of the dual-arm support fixedly connected to the handle member;
a release knob moveably connected to the handle member, the release knob having serrations; and
a ratchet gear mechanism having a first leg, a second leg and a tail,
the first leg of the ratchet-gear mechanism pivotably connected to the dual-arm support and further connected to the alignment drill-barrel,
the second leg of the ratchet-gear mechanism having pawls that engage the serrations when the ratchet gear mechanism selectively moves,
the tail of the ratchet gear mechanism operable by a user to selectively move the ratchet-gear mechanism,
wherein, movement of the ratchet-gear mechanism slides the alignment drill-barrel relative to the bushing to radially expand the forward end to releasably lock the bushing to the plate.

19. The drill-guide assembly, as recited in claim 18, wherein the dual-arm support is L-shaped.

20. The drill-guide assembly, as recited in claim 18, wherein the dual-arm support is fixed to the bushing by a method of fixing selected from the group consisting of welding, friction fitting, and press fitting.

21. The drill-guide assembly, as recited in claim 18, wherein the first part of the dual-arm support and the axial direction of the alignment assembly form an angle in the range of from about 75 degree to about 120 degree.

22. The drill-guide assembly, as recited in claim 18, wherein the second part of the dual-arm support and the first part of the dual-arm support form an angle in the range of from about 90 degree to about 150 degree.

23. The drill-guide assembly, as recited in claim 18, wherein the handle member has a front end and a back end, and wherein the dual-arm support and the handle member are fixedly connected at the front end of the handle member.

24. The drill-guide assembly, as recited in claim 18, wherein the dual-arm support is an integral, monolithic construction.

25. The drill-guide assembly, as recited in claim 18, wherein the second part of the dual-arm support and the handle member form an angle in the range from about 90 degree to about 150 degree.

26. The drill-guide assembly, as recited in claim 18, wherein the longitudinal axis of the handle member lies in the same plane as the longitudinal axis of the first part of the dual-arm support, and the longitudinal axis of the second part of the dual-arm support.

27. The drill-guide assembly, as recited in claim 18, wherein the longitudinal axis of the handle member is parallel to the longitudinal axis of the first part of the dual-arm support.

28. The drill-guide assembly as recited in claim 18, wherein the dual-arm support is immovably connected to the bushing at the proximal end of the bushing and the dual-arm support is immovably connected to the handle member.

29. The drill-guide assembly, as recited in claim 18, wherein the dual support has an open space and the ratchet gear mechanism is disposed in the open space and pivotally mounted therein.

30. The drill-guide assembly, as recited in claim 18, wherein the ratchet gear mechanism is Y-shaped.

31. The drill-guide assembly, as recited claim 30, wherein, the first leg of the ratchet-gear mechanism further extends beyond the pivot point forming a C-shaped vice-grip; wherein the C-shaped vice-grip grasps the alignment drill-barrel between two ridges on the alignment drill-barrel.

32. The drill-guide assembly, as recited claim 31, wherein the plane of the C-shaped vice-grip makes an acute angle with the longitudinal axis of the first leg of the Y-shaped ratchet-gear mechanism.

33. The drill-guide assembly, as recited claim 31, wherein the acute angle is in a range of from about 25 degree to about 45 degree.

34. The drill-guide assembly, as recited in claim 18, wherein the handle member is fixed to the dual-arm support with a pin that is perpendicular to the axis of the handle member.

35. The drill-guide assembly as recited in 18, wherein said expandable forward-end of said bushing is circular shaped, and freely insertable and removable from said bone plate fastener holes in a contracted position, and engaging the bone-plate when in an expanded position.

36. The drill-guide assembly as recited in 18, wherein said radially expandable forward-end comprises a plurality of finger portions.

37. The drill-guide assembly as recited in 36, wherein:
said radially expandable forward-end of the bushing comprises a shoulder, a neck, and an outwardly projecting rim disposed forward of said neck;
wherein said neck and rim together span a length that is slightly longer than the thickness of the bone plate fastener hole wall and the rim abuts the bone-side surface of said plate.

38. The drill-guide assembly, as recited in claim 37, wherein the handle member comprises a first cavity and a second cavity at the front end, wherein the first cavity houses a compression spring, and the second cavity houses the second part of the dual-arm support.

* * * * *

UNITED STATES PATENT AND TRADEMARK OFFICE
CERTIFICATE OF CORRECTION

PATENT NO.         : 7,357,804 B2                              Page 1 of 1
APPLICATION NO.    : 10/639515
DATED              : April 15, 2008
INVENTOR(S)        : Lawrence J. Binder, Jr. et al.

It is certified that error appears in the above-identified patent and that said Letters Patent is hereby corrected as shown below:

Column 12, line 29 reads -- The drill-guide assembly, as recited claim 30, -- should read -- The drill-guide assembly, as recited in claim 30, --.

Column 12, line 34 reads -- The drill-guide assembly, as recited claim 31, wherein -- should read -- The drill-guide assembly, as recited in claim 31, wherein --.

Column 12, line 38 reads -- The drill-guide assembly, as recited claim 31, wherein -- should read -- The drill-guide assembly, as recited in claim 31, wherein --.

Column 12, line 45 reads -- The drill-guide assembly as recited in 18, wherein said -- should read -- The drill-guide assembly as recited in claim 18, wherein said --.

Column 12, line 50 reads -- The drill-guide assembly as recited in 18, wherein said -- should read -- The drill-guide assembly as recited in claim 18, wherein said --.

Column 12, line 53 reads -- The drill-guide assembly as recited in 36, wherein: -- should read -- The drill-guide assembly as recited in claim 36, wherein: --.

Signed and Sealed this

Sixteenth Day of June, 2009

JOHN DOLL
*Acting Director of the United States Patent and Trademark Office*